(12) United States Patent
Hall (10) Patent No.: US 9,569,483 B2
(45) Date of Patent: Feb. 14, 2017

(54) PERSONALIZED DYNAMIC FEEDBACK CONTROL OF BODY WEIGHT

(71) Applicant: The United States of America, as represented by the Secretary, Department of Health and Human Services, Washington, DC (US)

(72) Inventor: Kevin Dennis Hall, Kensington, MD (US)

(73) Assignee: THE UNITED STATES OF AMERICA, AS REPRESENTED BY THE SECRETARY, DEPT. OF HEALTH AND HUMAN SERVICES OFFICE OF TECHNOLOGY TRANSFER, NATIONAL INSTITUTES OF HEALTH, Washington, DC (US)

( * ) Notice: Subject to any disclaimer, the term of this patent is extended or adjusted under 35 U.S.C. 154(b) by 154 days.

(21) Appl. No.: 13/754,058

(22) Filed: Jan. 30, 2013

(65) Prior Publication Data
US 2013/0198214 A1    Aug. 1, 2013

Related U.S. Application Data

(60) Provisional application No. 61/592,325, filed on Jan. 30, 2012.

(51) Int. Cl.
*G06F 19/00* (2011.01)
*G06F 17/30* (2006.01)

(52) U.S. Cl.
CPC ..... *G06F 17/30386* (2013.01); *G06F 19/3475* (2013.01); *G06F 19/3481* (2013.01)

(58) Field of Classification Search
CPC . G06F 19/3475; G06F 19/322; G01N 2800/52
(Continued)

(56) References Cited

U.S. PATENT DOCUMENTS 6,478,736 B1 * 11/2002 Mault ............................ 600/300
2002/0156351 A1 * 10/2002 Sagel ............................ 600/300
(Continued)

OTHER PUBLICATIONS

Thomas, D.M., A Computational Model to Determine Energy Intake During Weight Loss, Grant Submission, Award No. NIH 1R15DK090739-01A1, 2011.
(Continued)

*Primary Examiner* — Cheyne D Ly
(74) *Attorney, Agent, or Firm* — Polsinelli PC; Ron Galant (57) ABSTRACT

The present subject matter relates to a personalized weight management program incorporating dynamic feedback control using a validated mathematical model of metabolism and weight change. In general, the subject matter provides a system for repeated monitoring of one or more parameters such as, for example, body weight, physical activity, diet, eating behavior, or various other physiological and behavioral measurements, and using the parameter(s) to calculate an objective and personalized measure of adherence to a prescribed intervention, iteratively update mathematical model parameters, and adjust the prescribed intervention based on revised model predictions. Such a dynamic feedback control methodology can improve adherence to weight management interventions and result in greater weight loss and improved weight maintenance. The present subject matter also relates to a novel, cost-effective, weight management tool that could be widely disseminated through the internet and mobile computing platforms.

20 Claims, 6 Drawing Sheets

(58) Field of Classification Search
USPC .......................................... 702/19; 707/758
See application file for complete search history.

(56) References Cited

U.S. PATENT DOCUMENTS

| | | | |
|---|---|---|---|
| 2003/0187683 A1* | 10/2003 | Kirchhoff | G01G 19/4146 705/1.1 |
| 2005/0113650 A1* | 5/2005 | Pacione et al. | 600/300 |
| 2006/0015016 A1* | 1/2006 | Thornton | A61B 5/00 600/300 |
| 2006/0259323 A1* | 11/2006 | Chan | 705/2 |
| 2009/0131814 A1* | 5/2009 | Thompson | 600/561 |
| 2011/0053121 A1* | 3/2011 | Heaton | A61B 5/14532 434/127 |
| 2011/0184898 A1* | 7/2011 | Lan | G06N 3/08 706/21 |
| 2013/0132319 A1* | 5/2013 | Landers | G06N 5/02 706/46 |
| 2014/0128691 A1* | 5/2014 | Olivier | 600/301 |

OTHER PUBLICATIONS

Thomas, D.M., NIMBioS Investigative Workshop Mathematical Models of Metabolism and Body Weight Regulation, 2011.

Thomas, Dr. Diana, A Computational Model of Weight Change Resulting from Reduced Physical Activity, Margaret and Herman Sokol Fellowship, 2010.

Thomas, D.M., Martin C.K., Heymsfield S.B., Redman L.M., Schoeller D.A., Levine J.A., A Simple Model Predicting Individual Weigh Change in Humans, Journal of Biological Dynmaics. 1:1-7, Feb. 2011.

Thomas, D.M., Schoeller D.A., Redman L.M., Martin C.K., Levine J.A., Heymsfield S.B., A Computational Model to Determine Energy Intake During Weight Loss, Am J Clin Nutr. Dec. 2010; 92(6):1326-31. Epub 2010.

Thomas, D.M.; Presenter. Mathematical Body Weight Regulation Models from Bench to Bedside, 2011.

Martin, Corby; Presenter. Clinical Application of Models that Quantify Dietary Adherence from Body Weight, 2011.

Martin, Corby, Design and Evaluation of the Remote Intervention for Diet and Exercise (RIDE). Grant Submission, NIH Award No. 1R03DK083522-1, 2008.

Martin, Corby; Presenter. Mathematical Models of Metabolism and Body Weight Regulation. NIMBioS Investigative Workshop (Jul. 12-15, 2011).

Thomas, D.M.; Presenter. New Fat Free Mass Model, International Conference on Obesity, Stockholm, Sweden, Jul. 2010.

Trabulsi, Jillian and Schoeller, Dale, Evaluation of Dietary Assessment Instruments Against Doubly Labeled Water a Biomarker of Habitual Energy Intake, Department of Nutritional Sciences, University of Wisconsin-Madison, AJP-Endocrinol Metab, Nov. 2001.

Schoeller, Dale A., How Accurate Is Self-Reported Dietary Energy Intake?, Nutrition Reviews, vol. 48, No. 10, Oct. 1990. 373-379.

Hall, Kevin D., Modeling Metabolic Adaptations and Energy Regulations in Humans, Annual Review Nutrition, 2012.32:35-54.

Hall, Kevin D. et al, Quantification of the effect of energy imbalance on bodyweight, Lancet 2011; 378:826-37.

Hall, Kevin D., Predicting metabolic adaptation, body weight change, and energy intake in humans, Am J Physiol Endocrinol Metab 298: E449-E466, 2010.

Thomas, Diana et al, A simple model predicting individual weight change in humans, Journal of Biological Dynamics, 5:6, 579-599. 2011.

Hall, Kevin D. et al, Estimating changes in free-living energy intake and its confidence interval, Am J Clin Nutr 2011;94:66-74.

Thomas, Diana M. et al, A computational model to determine energy intake during weight loss, Am J Clin Nutr 2010;92:1326-31.

* cited by examiner

PERSONALIZED DYNAMIC FEEDBACK CONTROL OF BODY WEIGHT

CROSS REFERENCE TO RELATED APPLICATIONS

This application claims the priority of U.S. provisional application No. 61/592,325, filed Jan. 30, 2012, the entire disclosures of which are hereby incorporated by reference.

GOVERNMENT INTEREST STATEMENT

The present subject matter was made with U.S. government support. The U.S. government has certain rights in this subject matter.

FIELD

The present subject matter relates generally to weight management systems, devices, and methods. More specifically, the present subject matter relates to systems, algorithms, device networks, and methods that provide a personalized dynamic weight loss or weight management program.

BACKGROUND

Obesity and diabetes have undergone explosive growth within almost every nation in the world. The medical profession, health maintenance organizations, and insurance companies have realized that this epidemic must be brought under control. Many corporations have implemented programs in to inspire employees to lose or control weight. Commonly, individuals struggle to find a diet or exercise plan that fit their needs and results in effective weight loss. Diet, physical activity, and exercise may each contribute to body weight management, but specifics and personalization are lacking regarding what is required to achieve and maintain an individual's ideal weight. Previous research has suggested that personalization and feedback may be useful aspects of web-based weight management programs and simple weekly feedback based on daily weight measurements may be effective at preventing weight gain for some individuals. While promising, these previous efforts made either limited or no use of personalization and feedback but rather used tools such as progress charts and journals which may be difficult for many individuals to maintain and use consistently. Thus, there remains a need for an easy to use personalized weight loss program.

SUMMARY

The present subject matter relates to a personalized weight management system for monitoring and managing the weight of an individual, or simultaneously monitoring and managing the weights of a group of individuals.

In one embodiment, the present subject matter relates to a personalized weight management system for monitoring and managing the weight of an individual, comprising: a weight sensing device for monitoring the individual's weight, the weight sensing device generating a parameter indicative of the individual's weight; a data base for storing the weight parameter, said data base comprising at least one record specific to the individual, the record including the weight parameter; means for communicating the parameter to the data base; means for retrieving the parameter from the data base; and a software function executing on a processor using a mathematical model of metabolism and weight change and providing repeated monitoring of the parameter, iterative recalculation of model parameters and predicted weight change, and directing one or more weight management procedures or activities to be carried out by the individual or weight management professional in response to the model calculations.

In another embodiment, the present subject matter provides a sensor providing measurement of a second parameter selected from at least one physiological measurement, at least one behavioral measurement, or a combination thereof. Non-limiting examples of a second parameter may be selected from the group consisting of metabolic heat production, body composition, oxygen consumption, carbon dioxide production, isotopic tracer dilution, isotopic tracer turnover, urinary metabolites, blood metabolites, blood hormone levels, physical activity, exercise, heart rate, blood pressure, food selection, diet adherence, eating behavior, step number, accelerometer data, sleep behavior, circadian rhythm, environmental temperature, geographical location, anthropometry measurements, and combinations thereof.

In a further embodiment, the weight management procedure comprises a prescribed intervention, wherein the intervention is selected from the group consisting of dietary selection, physical activity, exercise, psychological intervention, surgery, medication administration, alteration of sleep or circadian rhythmicity, or a combination thereof. One or more embodiments may be configured to monitor obesity therapy or adherence to a weight loss/intervention program. The weight management parameters of the individual may be optionally monitored at predetermined intervals.

In yet another embodiment, a system for monitoring and responding to the weight condition of a individual is provided, comprising: a first sensor for monitoring the individual's weight, the first sensor generating a first parameter indicative of the individual's weight; a second sensor for monitoring the individual's metabolic state, the second sensor generating a second parameter indicative of the individual's metabolic state; a recorder for storing the second parameter generated by the second sensor; a base device for storing the parameters generated by the first sensor and the recorder; a data base located at a remote location from the first and second sensors and the recorder, for storing parameters indicative of the individual's weight and metabolic state, said data base comprising at least one record specific to the individual, the record including the sensor parameters; a communications subsystem to transfer the parameters from the base device to the data base; a process to retrieve the parameters from the data base; and a software function executing on a processor for directing one or more weight management procedures or activities to be carried out by the individual in response to the retrieved parameters.

In another embodiment, the present subject matter provides a method for managing the weight of a group of individuals, each with their own personalized dynamic metabolism and weight change model, comprising: enlisting two or more individuals in a weight management group; monitoring each individual separately using one of the weight management systems described herein; creating a personalized mathematical model of metabolism and weight change for each individual; and providing one or more personalized weight management procedures or activities to be carried out by each individual in response to the retrieved parameters.

According to another aspect, a personalized weight management system is provided for monitoring and managing the weight of an individual. This aspect may include one or more of the following exemplary features. The system includes at least one processor and a data base for storing. The database includes a plurality of weight management records. Each weight management record corresponds to weight management data for an individual or for each one of a plurality of individuals. The database also includes a personalized weight metabolism model record for an individual or for each of a plurality of individuals. Each personal weight metabolism model record corresponds to a particular mathematical model of metabolism for each one of the plurality of individuals. The system also includes a weight management application includes modules executable by the at least one processor to receive a weight management request. The weight management request includes current weight management data for a particular individual. The weight management application also retrieves a corresponding personal weight metabolism model for the particular individual from the data base in response to the management request. The personal weight metabolism model defines one or more expected weight parameter for the particular individual. The weight management application also calculates at least one new weight parameter for the corresponding personal weight metabolism model based on the current weight data. The weight management application also compares the new weight parameter to the expected parameter to determine an adherence status for the particular individual with a defined intervention program. The weight management application also generates a feedback signal. The feedback signal may comprise a display indicating the adherence status for the particular individual.

According to yet another aspect, a method is provided for monitoring and managing the weight of an individual. This aspect may include one or more of the following exemplary features. The method includes receiving a weight management request at at least one processor. The weight management request comprising current weight management data for a particular individual. The method also includes retrieving a corresponding personal weight metabolism model for a particular individual from a data base in response to the weight management request. The data base stores a plurality of personal weight metabolism model records. Each personal weight metabolism model record corresponds to a particular mathematical model of metabolism for an individual or for each of a plurality of individuals. The personal weight metabolism model defining one or more expected weight parameter for the particular individual. The method also includes calculating at least one new weight parameter at the at least one processor for the corresponding personal weight metabolism model based on the current weight data. The method also includes comparing the new weight parameter to the expected parameter at the at least one processor to determine an adherence status for the particular individual with a defined intervention program. The method also includes generating, a feedback signal. The feedback signal may comprise a display indicating the adherence status for the particular individual.

DETAILED DESCRIPTION

The present subject matter relates to a personalized weight loss or intervention program that incorporated dynamic feedback control using a mathematical model of human metabolism and weight change. In general, the subject matter provides a system for repeated monitoring of one or more parameters such as, for example, body weight, physical activity, diet, eating behavior, or various other physiological and behavioral measurements, and using the parameter(s) to calculate an objective and personalized measure of adherence to a prescribed intervention, iteratively update mathematical model parameters, and adjust the prescribed intervention based on revised model predictions. Such a dynamic feedback control methodology can improve adherence to weight management interventions and result in greater weight loss and improved weight maintenance. The present subject matter also relates to a novel, cost-effective, weight management tool that could be widely implemented through the internet and mobile computing platforms.

Relationship Between Diet and Weight Loss in Obesity

The prevalence of obesity has reached epidemic proportions and the incidence and economic burden of obesity-related complications are rapidly increasing. While obese individuals often attempt to lose weight through diet and exercise, they generally fail to meet their goals and weight regain is common. These failures may be due to difficulties in setting appropriate goals for weight loss as well as vague or erroneous information regarding the caloric deficit necessary to achieve and maintain a given weight loss.

For example, quantifying the relationship between calorie balance and body weight change has been difficult and the prior art either presumes a qualitative relationship between calories and weight or adopts widespread official recommendations from the National Health Service in the Deviceed Kingdom, the NHLBI, and the American Dietetic Association which state that reducing energy intake by ~500 kcal/d will result in slow and steady weight loss of about 0.5 kg each week. The basis of this recommendation is the ubiquitous dieting rule that "3500 kcal equals 1 pound" which has been used for more than half a century to estimate expected weight loss in humans. But despite its popularity, the assumptions underlying this calculation are now known to be invalid because it ignores important physiological adaptations to altered body weight that lead to changes of both resting metabolic rate as well as the energy cost of physical activity. Hence, the official recommendations drastically overestimate the magnitude of expected weight loss making it difficult to accurately prescribe a lifestyle intervention that will achieve a weight loss goal in a specified time frame. Furthermore, such simple weight loss rules do not account for individual differences in metabolism and the response to weight control interventions. To address this issue, mathematical models of human metabolism have been developed and validated that are personalized and accurately simulate the dynamic changes of energy expenditure and body composition during weight loss. These models can be used to predict the weight loss time course in response to a given diet and exercise intervention and can thereby be used to help set body weight goals that are quantitatively commensurate with an agreed upon intervention. The present subject matter employs one or more of such models to create a personalized weight loss program that additionally incorporates dynamic feedback control using a personalized mathematical model of metabolism and weight change.

DEFINITIONS

For the purposes of this application, the following terms will have the following meanings unless specifically stated otherwise:

The phrase "weight management" as used herein means a method of attaining or maintaining a desired body weight, body composition (non-limiting examples include body fat percentage, muscle mass, subcutaneous fat mass, visceral fat mass), anthromometric measurements, or combinations thereof. Non-limiting examples of methods of weight management may be selected from the group consisting of inducing satiety (e.g., controlling or curbing appetite), effecting the reduction of food (e.g., caloric) intake, effecting weight loss, inhibiting weight gain, maintaining weight, and combinations thereof. A "weight management record" as used herein means a collection of weight management data for an individual or for each one of a plurality of individuals, wherein non-limiting examples of these data may include one or more prescribed weight management methods, body weight measurements, age, sex, height, time, anthropometry measurements, metabolic heat production, body composition, oxygen consumption, carbon dioxide production, isotopic tracer dilution, isotopic tracer turnover, urinary metabolites, blood metabolites, blood hormone levels, physical activity, exercise, heart rate, blood pressure, food selection, diet adherence, eating behavior, step number, accelerometer data, sleep behavior, circadian rhythm, environmental temperature, geographical location, and combinations thereof.

The term "BMI" means body mass index, which is an individual's weight divided by their height squared ($kg/m^2$).

The term "overweight" or "underweight" means a state significantly different from an optimal weight, body composition, anthromometry, or combinations thereof for a given individual. Definitions may vary widely, but for general purposes, an individual having a BMI of between about 25 and about 29.9 $kg/m^2$ will be considered to be overweight, whereas an individual having a BMI less than 18.5 kg/m2 will be considered to be underweight.

The term "obesity" means the state of being severely overweight or to have severe excessive weight. Definitions may vary widely, but for general purposes, a patient having a BMI of greater than about 30.0 $kg/m^2$ will be considered obese. The invention is not affected by the exact definition of obesity as stated by the current BMI standard and all such definitions are to be considered as equivalents.

The term "personalized" as used herein means an action or therapy that is designed or calculated with specific individualized parameters from an individual. A "weight metabolism model" as used herein means a mathematical model that predicts future changes in weight, body composition, anthrompometry measurements, or combinations thereof for an individual or for each of a plurality of individuals from the weight management records, interventions, or combinations thereof.

The term "feedback" as used herein to describe the situation where the output of a system in the past is used to influence the input to the system and modify its output in the present or the future. The term "dynamic" as used herein means a process affected by time. A dynamic process will continue to be dynamic by refreshing the data input and/or data output. The phrase "dynamic feedback" as used herein means that the process evolves with time based on repeated monitoring of the system output to adjust the input signal that is fed back to the system. The phrase "dynamic feedback control" means to adjust the input signal with the aim to control the system output to a desired result over time. The dynamic feedback control process involves calculating a prediction of at least one system output of interest (such as body weight), dynamically monitoring the system output, use the past measurements of system output to recalculate the prediction of future system output, calculate a "feedback signal" to be provided as system input to control the future system output to attain a desired result.

The phrase "mathematical model parameters" as used herein means the numerical values used in algorithms designed to reflect body weight gain and body weight loss.

The phrase "estimated model uncertainty range" as used herein means the calculated probable range of future system output.

The phrases "iteratively update" and "iteratively calculate" are interchangeable and as used herein mean to re-calculate one or more model parameters based on past measurements of the system output.

Some individuals may require an intervention to achieve weight management. The term "intervention" as used herein means an activity or set of activities aimed at modifying a process, course of action or sequence of events, (non-limiting examples include diet change, exercise, psychological counseling, surgery, medication administration, alteration of sleep or circadian rhythmicity, or a combination thereof) in order to change one or several outcomes. Non-limiting examples of outcomes include body weight, metabolic heat, satiety, hunger, physical activity, or combinations thereof.

The term "adherence" as used herein means following an intervention to attain the desired weight management goals. If the intervention is not followed, it is likely that the actual body weight will veer from the predicted body weight and the body weight management goal will not be met.

Out-Patient Weight Loss and Maintenance Programs

Figure 1:
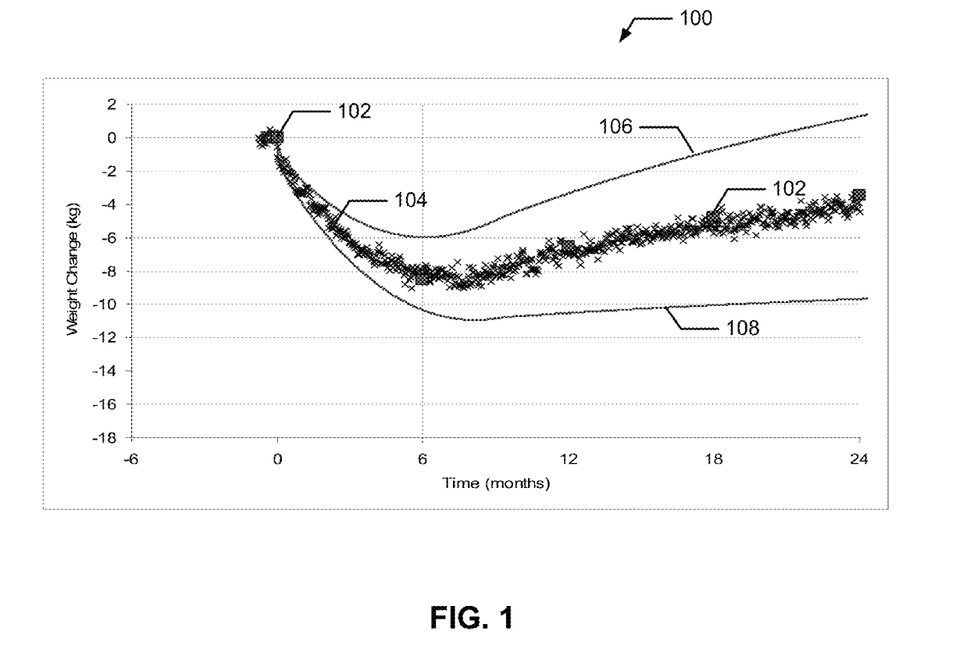
FIG. 1 depicts a chart of an exemplary out-patient weight change trajectory according to current standard of care.

FIG. 1 is a chart 100 that depicts a typical out-patient weight change trajectory points 102 along with a model-simulated weight changes 104 in an individual eating the average energy intake with the estimated relaxation of diet adherence. The upper and lower precision estimate curves 106, 108, respectively, depict the estimated model uncertainty range based on a 5% precision of measuring baseline energy requirements using the doubly labeled water method Out-patient weight loss interventions typically result in a maximum weight loss after ~6-8 months followed by gradual weight regain over subsequent years (e.g., see FIG. 1). The question of what change of dietary energy intake would be required to reproduce a typically observed weight loss and regain trajectory was previously investigated and results suggested that the adherence to the prescribed diet was not constant—an interpretation supported by previous research demonstrating that total energy expenditure is much higher than self-reported energy intake at the weight loss plateau. The results of mathematical model simulations showed that the observed average weight changes could only have occurred if adherence to the initial ~750 kcal/d reduction of dietary energy intake was rapidly and progressively relaxed such that the patients returned to their original weight maintenance diet within the first year where it then stayed for the remainder of the simulation. This is a typical weight change trajectory for obese patients undergoing an out-patient weight loss intervention. The present subject matter describes a methodology for generating accurate personalized weight change predictions for a prescribed intervention using mathematical models of human metabolism and subsequently calculate adherence to the intervention as well as iteratively update model parameters and adherence metrics over time using physiological and behavioral measurements. For the first time, we show how such dynamically updated model simulations can be used to provide quantitative feedback regarding adherence to the intervention as well as quantitative guidance on any modification of the intervention required to achieve the weight goal. This personalized dynamic feedback control method will thereby allow for improved intervention adherence and personalized management of body weight than was previously possible.

Weight Loss Programs Incorporating Personalization and Feedback

Previous research has shown that personalization and feedback are often useful aspects of web-based weight loss programs and simple weekly feedback by telephone, mail or email based on daily body weight measurements has been effective at preventing weight gain in some individuals. While promising, these previous efforts have made limited use of personalization and feedback but rather used tools such as progress charts and journals which may be difficult for many individuals to maintain and use accurately and consistently. Furthermore, prior art has been unable to provide accurate quantitative prescriptions for the impact of an intervention on an individual's body weight since they fail to account for changes of metabolism that occur with weight change.

Herein, the first personalized weight loss program is described incorporating dynamic feedback control using an accurate personalized mathematical model of metabolism and weight change in combination with repeated physiological or behavioral measurements such as body weight, physical activity, diet, eating behavior, various components of energy expenditure, metabolic heat production, or combinations thereof. The present personalized weight loss program differs substantially from prior art in that personalized mathematical models of metabolism are used to accurately simulate an individual's metabolism as their weight changes and the model parameters are iteratively and dynamically updated based on repeated physiological or behavioral measurements. The updated model simulations are thereby used to provide ongoing dynamic and quantitative feedback regarding adherence to the intervention, the projected body weight trajectory range, and quantitative guidance regarding any modifications to the intervention required to achieve weight goals. The weight goals can also be dynamically updated during the course of the feedback control intervention.

Figure 2:
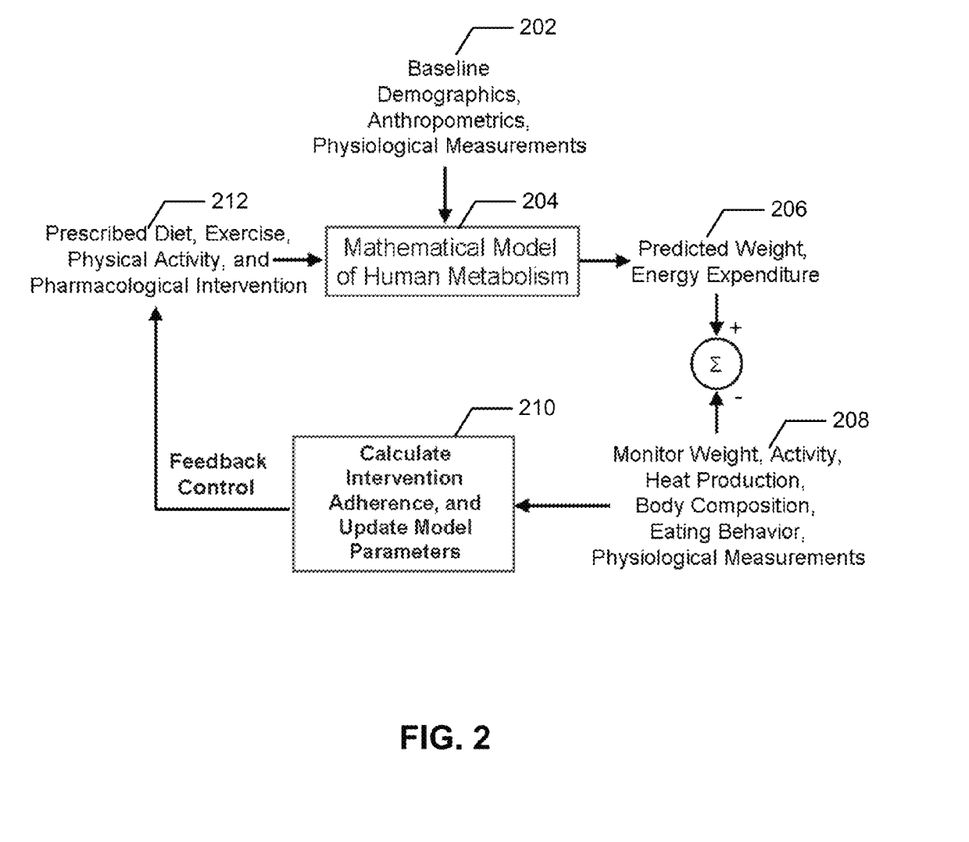
FIG. 2 is a process flow depicting a method for implementing weight-loss interventions according to an aspect of the personalized weight management system.

FIG. 2 depicts an exemplary dynamic feedback control method for weight loss and weight maintenance according to one aspect of the personalized weight loss system. In one embodiment, baseline metabolic and anthropomorphic data are collected to personalize a mathematical model of metabolism for each individual at 202. The personalized metabolism model is then applied to baseline metabolic and anthropomorphic data at 204 and used to set realistic weight loss goals through an intervention program at 206. Progress is monitored by collecting repeated body weight measurements which can be used along with other physiological and behavioral measurements (e.g., physical activity monitors, resting metabolic rate, heat production, temperature) at 208 to calculate dietary changes using various methodologies, such as the method described in *Estimating changes in free-living energy intake and its confidence interval*, Hall K D et al. Am J Clin Nutr. 94(1): 66-74, 2011, incorporated herein in its entirety by reference, as well as other intervention adherence metrics at 210. The calculated intervention adherence can be used to assess progress, provide early warning alerts if the adherence is waning, and along with the optional measurements of physiological and behavioral data, may be used to iteratively update the mathematical model parameters of the present subject matter to improve the accuracy of the personalized model and project whether the individual is on track to meet their goal weight. At 212, feedback reports can be periodically generated and provided to the individual or the weight management professional describing their calculated adherence to the intervention, their projected weight loss trajectory range if they continue at their current level of adherence, and quantitative prescriptions for specific modifications to the intervention that are required to achieve their goal weight. Modifications to the goal weight can also be updated iteratively as the dynamic feedback control intervention progresses.

Figure 3A:
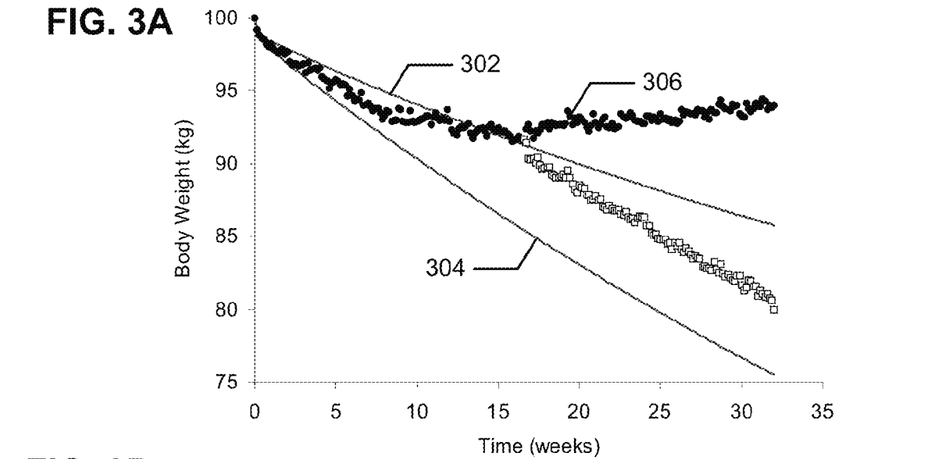
FIG. 3A-3C depict body weight changes and energy intake changes that occur during a simulated weight loss program according to one aspect of the personalized weight management system.
Figure 3B:
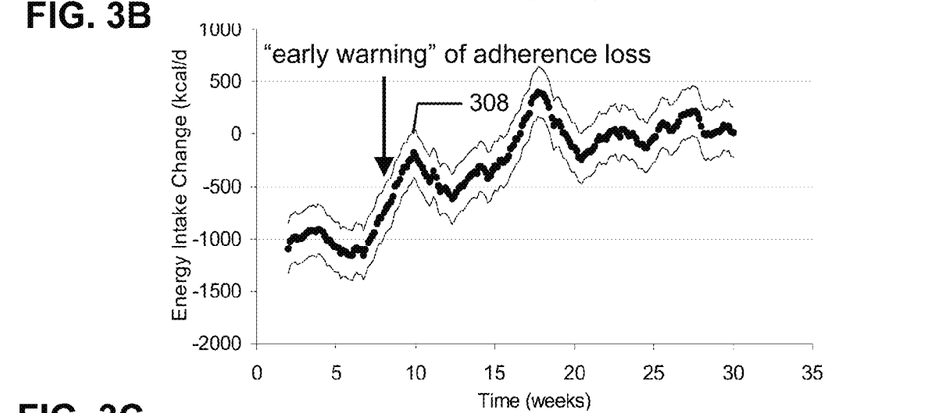
Figure 3C:
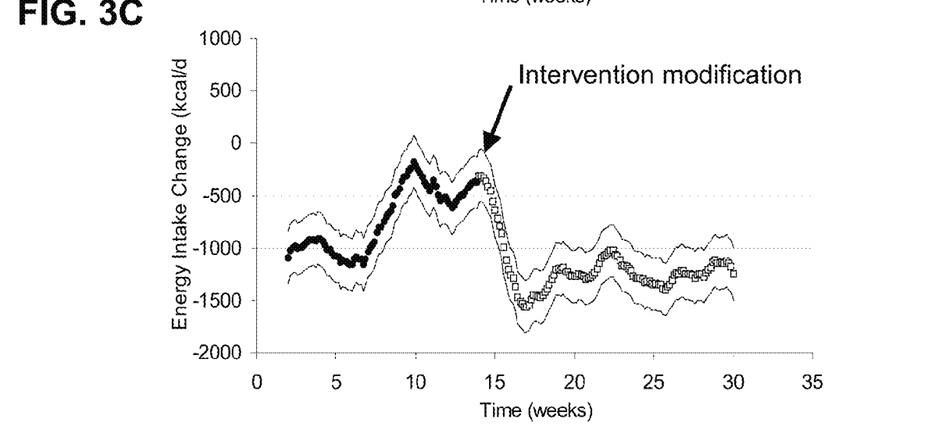

FIG. 3A-C depict body weight changes and energy intake changes that occur during a simulated 32 week weight loss program in a 100 kg male subject according to one aspect of the personalized weight loss control system. In this example, the initially prescribed diet intervention for the subject was designed so that his body weight should fall within the goal weight range between the upper and lower curves 302, 304, respectively, shown in a body/weight chart in FIG. 3A using a personalized mathematical model. In this example, the prescribed intervention was to reduce the diet by 1000±100 kcal/d to achieve a goal weight loss of 20±5 kg after 32 weeks. The black circles 306 depict the weight measurements when the diet was reduced by ~1000 kcal/d for the first several weeks, followed by a progressive loss of diet adherence 308 as shown in FIG. 3B that would likely occur in the absence of dynamic feedback control. The calculated diet changes (e.g., see FIG. 3B) allow for periodic feedback messages to be delivered providing early warnings of adherence loss and revised weight predictions. The mathematical model parameters will be iteratively updated based on the ongoing measurements of weight and other parameters. FIG. 3C illustrates that due to the loss of adherence to the intervention prior to week 14 a further 200 kcal/d reduction of dietary energy intake from the original prescribed diet was calculated be required to reach the goal weight. Feedback messages on the required modified intervention were delivered after week 14 and improved adherence to the new diet prescription (e.g., see FIG. 3C) allowed the person to achieve their weight goal (e.g., see FIG. 3A). The calculated improved adherence to the revised diet intervention after week 14 showed that the dieter was on target after week 15. This example is for illustrative purposes only and the frequency of feedback messages as well as calculated thresholds and timing of intervention modifications can vary as will be clear to an individual skilled in the art.

Computerized Personalized Weight Management System

Aspects of a personalized weight management system (PWMS) described herein provide an improved system and method for implementing weight-loss interventions. The PWMS uses a baseline mathematical model of the metabolism of a subject or individual participating in a weight management intervention to prescribe dietary, physical activity guidelines, medication, surgery, and or other interventions for the subject to achieve a desired body weight or to be within a desired weight range over a period time. Thereafter, the PWMS periodically receives, for example, body weight data, physical activity data, diet data, eating behavior data, or various other physiological, and behavioral measurement data, for a subject and uses the mathematical model of the metabolism to predict a body weight for the subject. The PWMS compares an expected body weight of the subject to received body weight data to determine if the subject is adhering to the prescribed intervention. Other aspects of the PWMS dynamically update parameters of the mathematical model of the metabolism of a subject or individual and determine an updated intervention prescription to for the subject to achieve the desired body weight or to be within the desired weight range.

Figure 4A:
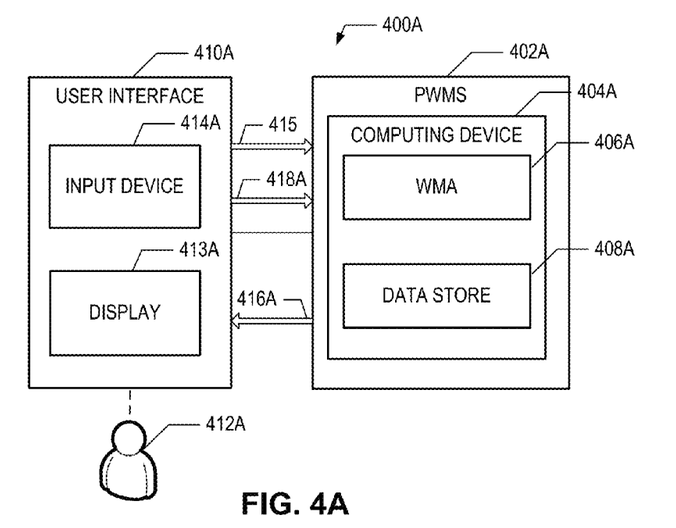
FIG. 4A-4C are a block diagram of computing systems that includes personalized weight management systems.

FIG. 4A depicts an exemplary computing network 400A that includes a PWMS 402A in accordance with aspects of the invention. The PWMS 402A includes a computing device (computer) 404A that includes a weight management application (WMA) 406A and a data store 408A. Although the data store 408A is shown as being located on, at, or within the computer 404A, it is contemplated that the data store 408A can be located remotely from the computer 404A in other aspects of the PWMS 402A, such as on, at, or within a database of another computing device or system having at least one processor and volatile and/or nonvolatile memory.

A user-interface (UI) 410A is linked to the PWMS 402A to enable a user 412A to submit weight data and/or energy intake data to the PWMS 402A for processing by the WMA 406A. According to one aspect, the UI 410A includes a display 413A, such as a monitor, for displaying one or more input forms, and an input device 414A, such as a keyboard or a pointing device (e.g., a mouse, trackball, pen, or touch screen), for entering data for a particular user 112 into one or more data input forms (not shown). For example, the user 412A interacts with data input forms via the user interface 410A to enter subject identification data, body weight data, and/or energy intake data and to generate a weight management request 415A. The subject identification data may include as a username, a password, pass code, or any other data that uniquely identifies a particular subject or individual participating, for example, in a weight management or intervention program. The computer 404A includes one or more processors and memory and is configured to receive data from and/or transmit data to the UI 410A. According to one aspect, the computer 404A receives the weight management request 415A from the UI 410A. The weight management request 415A includes, for example, subject identification data, body weight data and/or energy intake data enter by the user 412A via UI 410A.

As described in more detail below, the computer 404A executes the WMA 406A to dynamically update a personalized weight loss model for a particular subject in response to the weight management request 415A. The WMA 406A and transmits a weight management feedback signal 416A to the UI 410A. The weight management feedback signal 416A can be in the form of a message or generated report, or another communication that informs the subject of dietary management program adjustments and/or behavior adjustments, describes the subject's adherence to the intervention, shows the projected weight loss trajectory range at the subject's current level of adherence, and provides quantitative prescriptions for specific modifications to the intervention required to achieve their goal weight, or combinations thereof.

According to another aspect, the user may enter a modified weight management request (not shown) for processing by the WMA 406. The modified weight management request is, for example, substantially the same as the weight management request 415A except that it may include modified weight goal data. For example, after receiving weight management feedback signal, the user may decide to modify a body weight goal or the time allotted to achieve the goal, or combinations thereof.

Figure 5:
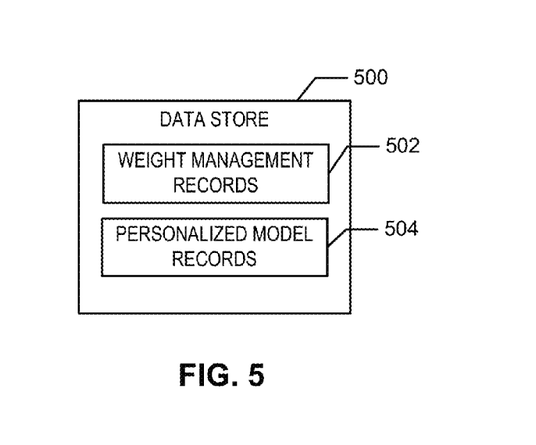
FIG. 5 depicts an exemplary embodiment of a data source according to an aspect of the personalized weight management system.

The WMA 406A is also configured to store subject data, body weight data, energy intake data, and weight interventional adherence data in the data store 408A. FIG. 5 depicts an exemplary embodiment of a data store 500 (e.g., data store 408A) according to one aspect of the PWMS 402A. The data store 500 stores weight management records 502 and personalized metabolism model records 504.

Each weight management record 502 includes subject data. Example subject data may include the name of a participant in a weight management program, an account number assigned to the participant, an email address, a phone number, a mailing address, and other contact information for the participant.

Each weight management record 502 also includes body weight data, energy intake data, weight interventional adherence data, and date/time data associated with particular subject data. For example, a particular weight management record 502 includes body weight data and energy intake data received at the PWMS 402A for a particular subject and includes weight interventional adherence data generated by the WMA 406A for that particular subject based on the received body weight data and energy intake data.

The time/data included in a particular weight management record 502 corresponds to a time the body weight data and/or energy intake data was received at the WMA 406A. According, because the PWMS 402A can be used to collect data over a period of time. Accordingly, the data store 500 may include multiple weight management records 502 that correspond to the same subject but include different date/time data.

Each of personalized model records 504 includes a personalized mathematical model of metabolism associated with a particular subject. As described above, a personalized mathematical model can be developed for a particular subject based on baseline metabolic and collected anthropomorphic data from that particular subject.

Figure 4B:
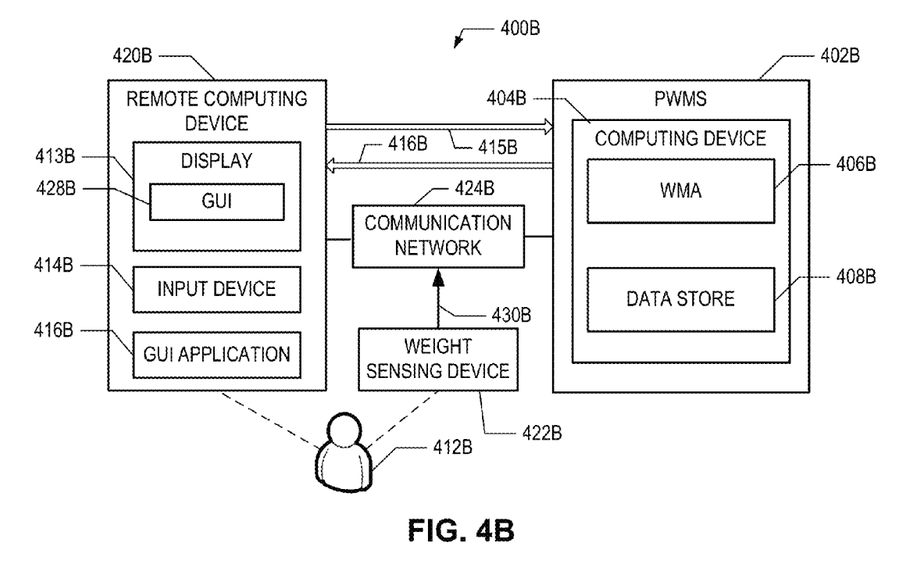

FIG. 4B depicts an exemplary computing network 400B that includes PWMS 402B in accordance with another aspect of the invention. The PWMS 402B includes a computer 404B that includes a WMA 406B and a data store 408B. The PWMS 402B is linked to one or more remote computing devices (e.g., remote computer) 420B and is linked to one or more weight sensing devices 422B via a communication network 424B.

The PWMS 402B is configured and operates substantially the same as the PWMS 402A described above in connection with FIG. 4A. In this aspect, however, the computer 404B is further configured to transmit data to and receive data from the remote computer 420B through the communication network 424B. The computer 404B is also configured to receive data from the weight sensing device 422B through the communication network 424B.

The communication network 424B can be the Internet, an intranet, or another wired or wireless communication network. For example, communication network 112 may include a Mobile Communications (GSM) network, a code division multiple access (CDMA) network, 3rd Generation Partnership Project (3GPP), an Internet Protocol (IP) network, a Wireless Application Protocol (WAP) network, a WiFi network, or an IEEE 802.11 standards network, as well as various combinations thereof. Other conventional and/or later developed wired and wireless networks may also be used.

According to one aspect, the one or more remote computers 420B are computing devices, such as a personal computer, a lap top computer, a personal digital assistant, or other computer. Each remote computer 420B may also include a graphical user interface (or GUI) application 428B, such as a browser application, to generate a graphical user interface 428B on the display 413B. The graphical user interface 428B enables a user of the remote computer 420B to interact with various data entry forms via an input device 414B to submit body weight data, energy intake data via a weight management signal 415B to the PWMS 402B for processing by the WMA 406B. For example, the WMA 406B updates the personalized weight loss model for a particular subject in response to the body weight data, energy intake data. The WMA 406B transmits a weight management feedback signal 416B to the remote computing device. For purposes of illustration, the weight management signal 415B and weight management feedback signal 416B are depicted in FIG. 4B as being transmitted directly between PWMS 402B and the remote computing device 420B. However, it is contemplated that the weight management signal 415B and weight management feedback signal 416B are transmitted between PWMS 402B and the remote computing device 420B via the communication network the 424B.

According to another aspect, the weight sensing device 422B is configured to collect, store, and communicate body weight data for a subject. Each weight sensing device 422B is configured to generate a weight measurement signal, as indicated by reference characters 430B, that comprise measurement data representative of one or more body weight parameter values regarding a particular subject. For example, the weight sensing device 422B is a weight scale that is configured to measure body weight of a subject and generates the weight measurement signal 430B comprising measurement data representative of the subject's body weight and communicates the measurement signal 430B to the PWMS 402B via the communication network 424B. Other examples of weight sensing devices 422B exist.

According to another aspect, the weight measurement signal 430B generated by the weight sensing device 422B includes a weight sensing device ID. The weight sensing device ID is an identification of a particular weight sensing device 422B and is unique to that particular weight sensing device 422B. The weight sensing device ID is used by the WMA 406B to accurately identify the weight sensing device 422B and identify a particular subject associated with that that particular weight sensing device 422B. For example, the data store 408B stores a data table (not shown) that includes a list of weight sensing device IDs and subject data associated with each weight sensing device ID. The WMA 406B queries the data table to identify the subject data that corresponds to a received weight sensing device ID.

The weight sensing device 422B may be connected to the communication network 424B via a wired connection or a wireless connection to transmit the weight measurement signal 430B to the PWMS 402B. According to another aspect, the weight sensing device 422B includes wireless transmitter (not shown) that transmits the weight measurement signal 430B. A wireless receiver (not shown) is connected to the PWMS 402B and receives the weight measurement signal 430B from the weight sensing device 422B.

The transmitter and corresponding receiver may utilize a Gigabit Ethernet link, IEEE 802.11 link, Ultra-Wide Band (UWB) link, or any other suitable wireless communication link. The wireless transmitter and wireless receiver are optional in some embodiments.

Figure 4C:
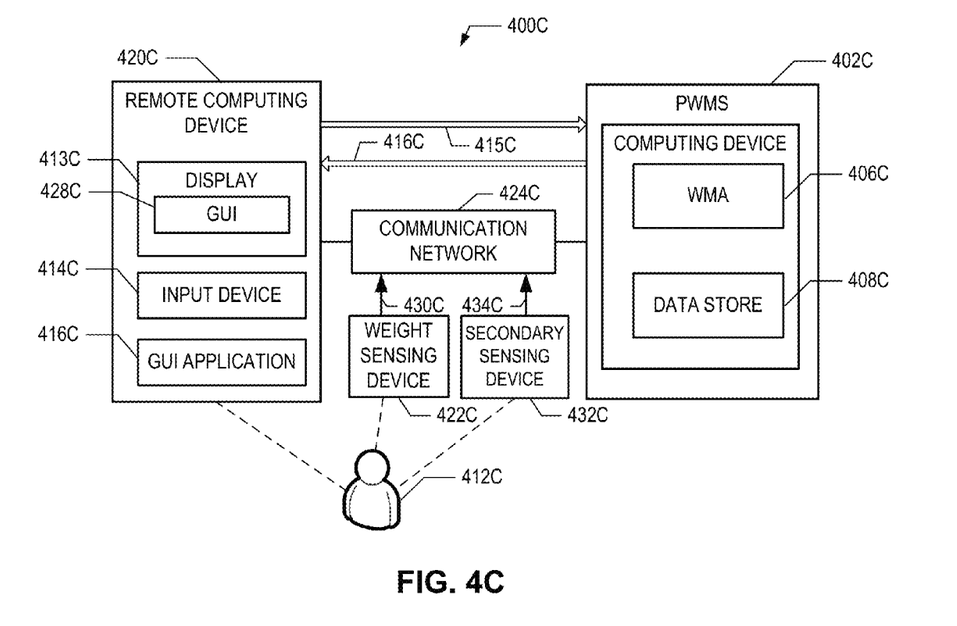

FIG. 4C depicts an exemplary computing network 400B that includes PWMS 402C in accordance with another aspect of the invention. The PWMS 402C includes a computer 404C that includes a WMA 406C and a data store 408C. The PWMS 402C is linked to one or more remote computing devices (e.g., remote computer) 420C, 424C and is linked to one or more weight sensing devices 422C and one or more secondary sensing devices 432C via a communication network 424C.

The PWMS 402C is configured and operates substantially the same as the PWMS 402A and PWMS 402C described above in connection with FIGS. 4A and 4B, respectively. The remote computer 420C is configured to operate substantially the same as the remote computer 420B described above in connection with FIG. 4B. In this aspect, however, the computer 404C is further configured to receive data from the secondary sensing device 432C through the communication network 424B.

According to another aspect, a secondary sensing device 432C is configured to collect, store, and communicate energy expenditure data for a subject. Each secondary sensing device 432C (or energy sensing device) is configured to generate an energy expenditure signal, as indicated by reference characters 434C, that comprise measurement data representative of one or more energy expenditure parameter values, such as physical activity, resting metabolic rate, heat production, and temperature, regarding a particular subject. Examples of secondary sensing devices 432C include a motion sensor, a heart rate monitor, and a body heat sensor. Other examples of secondary sensing devices 432C exist.

According to one aspect, the secondary sensing device 432C is a motion sensor, such as an accelerometer, that generates a signal that comprises motion data representative of motion sensed of a subject during a period of walking, running, or eating. For example, the secondary sensing device 432C may be attached near the jaw, throat, wrist, or hand of a subject and configured to detect eating or bite motions. In this example, secondary sensing device 432C generates the food intake signal 434C comprising data representative of the number of bites, chews, and swallows a subject's has taken over a period of time and communicates the food intake signal 434C to the PWMS 402C via the communication network 424C.

According to another aspect, the signal 434C generated by the secondary sensing device 432C includes a secondary sensing device ID. The secondary sensing device ID is an identification of a particular secondary sensing device 432C and is unique to that particular secondary sensing device 432C. The secondary sensing device ID is used by the WMA 406C to accurately identify the secondary sensing device 432C and identify a particular subject associated with that that particular secondary sensing device 432C. For example, the data store 408C stores a data table (not shown) that also include a list of secondary sensing device IDs and subject data associated with each secondary sensing device ID. The WMA 406C queries the data table to identify the subject data that corresponds to a received secondary sensing device ID.

The secondary sensing device 432C may be connected to the communication network 424C via a wired connection or a wireless connection to and configured to transmit the signal 434C to the PWMS 402C at predetermined time intervals (e.g., hourly, daily, weekly, etc.). The secondary sensing device 432C may also be configured to transmit the signal 434C to the PWMS 402C at user selected intervals.

According to one aspect, secondary sensing device 432C includes wireless transmitter (not shown) that transmits the signal 434C. A wireless receiver (not shown) is connected to the PWMS 402C and receives the signal 434C from the secondary sensing device 432C. The transmitter and corresponding receiver may utilize a Gigabit Ethernet link, IEEE 802.11 link, Ultra-Wide Band (UWB) link, or any other suitable wireless communication link. The wireless transmitter and wireless receiver are optional in some embodiments.

According to another aspect, the weight sensing device 422B and the energy sensing device (i.e., secondary sensing device 432C) operate as remote computing devices. For example, in addition to sensing body weight data and energy expenditure data, the PWMS 402C can be linked directly to the weight sensing device and/or the energy sensing device (i.e., secondary sensing device) to receive body weight data and energy expenditure data via the communication network 424C.

Figure 6:
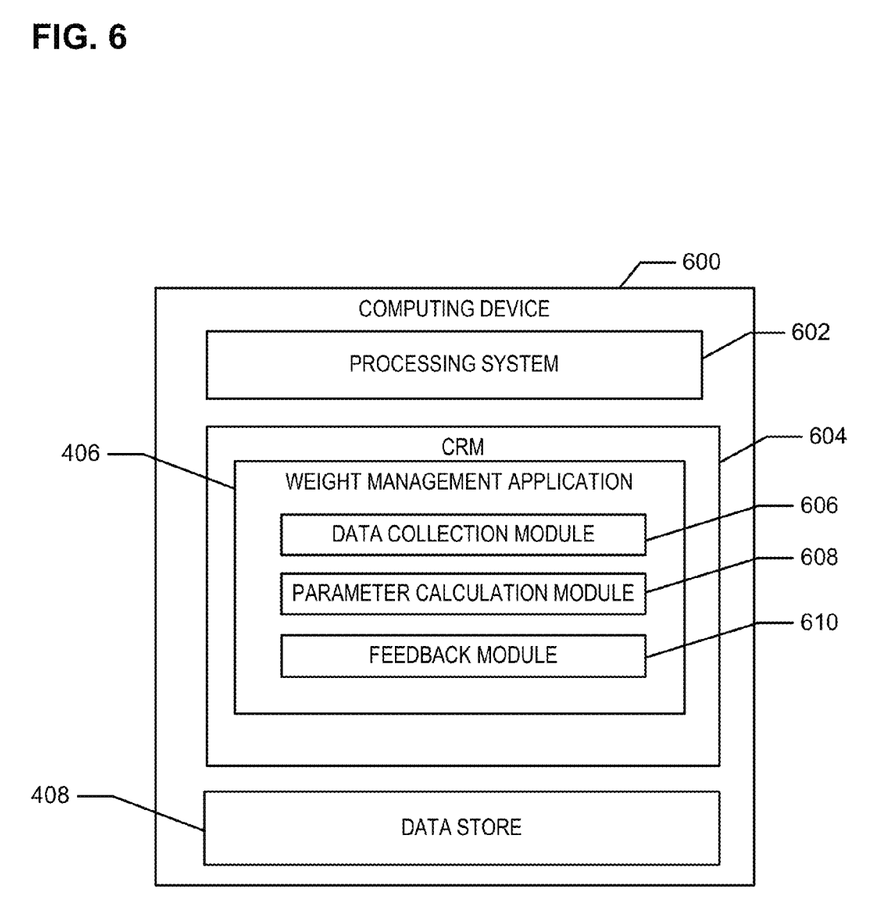
FIG. 6 a block diagram of a computing device configured with an weight management application according to one aspect of the personalized weight management system.

FIG. 6 is a block diagram that depicts a WMA 406 (e.g. 406A-406C) executing on a computing device 600 (e.g., computing device 404A-404C). According to one aspect, the computing device 600 includes a processing system 602 that includes one or more processors or other processing devices. The processing system 602 executes the WMA 406 to receive body weight data and/or energy intake data for a subject and generate a weight management feedback signal for transmission to the subject.

According to one aspect, the computing device 600 includes a computer readable medium ("CRM") 604 configured with the WMA 406. The WMA 406 includes instructions or modules that are executable by the processing system 602 to generate a weight management feedback signal for transmission to the subject via a local user interface (e.g., UI 410A) or via a remote computing device (e.g., 420B and 420C) in response to received body weight data and/or energy intake data.

The CRM 604 may include volatile media, nonvolatile media, removable media, non-removable media, and/or another available medium that can be accessed by the computing device 600. By way of example and not limitation, computer readable medium 604 comprises computer storage media and communication media. Computer storage media includes memory, volatile media, nonvolatile media, removable media, and/or non-removable media implemented in a method or technology for storage of information, such as computer readable instructions, data structures, program modules, or other data. Communication media may embody computer readable instructions, data structures, program modules, or other data and include an information delivery media or system.

A data collection module 606 is configured to identify subject data, body weight data and/or secondary physiological and/or behavioral data included in a received weight management request (see FIG. 4A). Alternatively, the data collection module is configured to identify body weight data and/or secondary physiological and/or behavioral data included in a received weight measurement signal 430B and/or secondary signal 434C, respectively (e.g., see FIGS. 4B and 4C). The data collection module is also configured to identify subject data based on a weight sensing device ID or a secondary sensing device ID included in the weight measurement signal 430B and/or secondary signal 434C, respectively.

A parameter calculation module 608 retrieves a personalized mathematical model of metabolism associated with a subject from the data store in response to received, subject identification data, body weight data and/or secondary physiological and/or behavioral data. The personalized mathematical model may be a baseline personalized mathematical model defined during an evaluation of period of the subject and stored in the data store. Alternatively, the retrieved personalized mathematical model may have been previously modified as described below.

According to one aspect, a linearized version of personalized mathematical model is represented by the following equation:

$$\left[\frac{\eta_F + \rho_F + \alpha\eta_L + \alpha\rho_L}{(1-\beta)(1+\alpha)}\right]\frac{dBW}{dt} = \qquad (1)$$

$$\Delta EI - \frac{1}{(1-\beta)}\left[\frac{\gamma_F + \alpha\gamma_L}{(1+\alpha)} + \delta\right](BW - BW_0) - \frac{\Delta\delta}{(1-\beta)}BW;$$

where BW is the body weight, $\Delta EI$ is the change of EI from its initial energy balanced value, and $\gamma_L = 22$ kcal·kg$^{-1}$ d$^{-1}$ and $\gamma_F = 3.2$ kcal kg$^{-1}$ d$^{-1}$ are the regression coefficients relating resting metabolic rate compared with lean body mass and fat mass, respectively. The parameter $\beta=0.24$ accounts for the thermic effect of feeding as well as adaptive changes of energy expenditure during under- and overfeeding. The parameters $\eta_F=180$ kcal/kg and $\eta_L=230$ kcal/kg account for the biochemical efficiencies associated with fat and protein synthesis (16, 17), assuming that the change of lean body mass is primarily accounted for by body protein and its associated intracellular water. The parameter $\delta=10$ kcal·kg$^{-1}$ d$^{-1}$ represents the baseline physical activity of a relatively sedentary person with a physical activity level (PAL) of 1.5 and the parameter $\Delta\delta$ represents changes in physical activity. The parameter $\alpha$ represents the relation between changes of lean and fat mass $\alpha=dL/dF=C/F$, where $C=10.4$ kg is the Forbes parameter. For modest weight changes, $\alpha$ can be considered to be approximately constant with F fixed at its initial value $F_0$ (19). An estimate for $\Delta EI$ is obtained by rearranging Equation 1:

$$\Delta EI = \varepsilon(BW - BW_0) + \rho m + \frac{\Delta\delta}{(1-\beta)}BW; \qquad (2)$$

where m is an estimate of the rate of change of BW over the corresponding time interval t, the parameter $\rho$ is the effective energy density associated with the BW change, and $\varepsilon$ is parameter that defines how energy expenditure depends on BW, $$\rho = \frac{\eta_F + \rho_F + \alpha\eta_L + \alpha\rho_L}{(1-\beta)(1+\alpha)} \qquad (3)$$

and $$\varepsilon = \frac{1}{(1-\beta)}\left[\frac{\gamma_F + \alpha\gamma_L}{(1+\alpha)} + \delta\right]. \qquad (4)$$

The parameter calculation module calculates new parameter values for the received personalized mathematical model associated with a particular subject based on the received body weight data and/or secondary physiological and/or behavioral data. For example, the parameter calculation module calculates the new parameter values for Δδ and β to best fit the past body weight data and secondary physiological and/or behavioral data along with the estimated change of energy intake ΔEI. The parameter calculation module then updates the personalized mathematical model to include the new parameter values. The parameter calculation module stores the updated personalized mathematical model in the data store 408 (e.g. 408A-408C.)

A feedback module 610 compares the calculated new parameter values for the received personalized mathematical model with expected parameter values to determine an adherence status for the individual. For example, the adherence status may include a projection of whether the individual is on track to meet their goal weight. The adherence status may also include or identify one or more corrective dietary and/or physical activities to place the individual back on track to meet their goal weight, or combinations thereof.

The feedback module 610 transmits feedback reports the adherence status to the individual subject or the weight management professional for the individual subject. The feedback report may include charts or graphs that display the subject's adherence to the intervention program, the subject's projected weight loss trajectory range if they continue at their current level of adherence, and quantitative prescriptions for specific modifications to the intervention that are required to achieve the subject's goal weight, or suggested modifications to the goal weight or time allotted to achieve the goal, or combinations thereof.

According to one aspect, the feedback module 610 is responsive to feedback request receive from a user of the remote computer or an administrative user of the computer to transmit feedback reports for display via the UI or remote computing device. According to another aspect, the feedback module 610 is configured to automatically transmit feedback reports for display via the UI or remote computing device at predetermined time intervals (e.g., weekly, bi-weekly, monthly, etc).

While not necessary to implement the method, measurements of various physiological or behavioral quantities (e.g., heat production, physical activity, heart rate, eating behavior, sleep patterns, etc.) over the course of the intervention can also be optionally used to iteratively update model parameters allowing for further personalization of the mathematical model and thereby provide more accurate weight change predictions and improved dynamic feedback control prescriptions for weight management.

While the present subject matter has been described with reference to the above embodiments, it will be understood by those skilled in the art that various changes may be made and equivalents may be substituted for elements thereof without departing from the scope of the subject matter. In addition, many modifications may be made to adapt a particular situation or material to the teachings of the subject matter without departing from the essential scope thereof. Therefore, it is intended that the subject matter not be limited to the particular embodiment disclosed as the best mode contemplated for carrying out this subject matter, but that the subject matter will include all embodiments falling within the scope of the appended claims.

What is claimed is:

1. A personalized weight management system for monitoring and managing body weight, comprising:
    at least one processor;
    a data base for storing:
        a weight management record for an individual or for each one of a plurality of individuals, each weight management record corresponding to weight management data comprising current body weight for an individual; and
        a personal weight metabolism model record for an individual or for each one of a plurality of individuals, each personal weight metabolism model record corresponding to a particular mathematical model of metabolism that predicts future changes in weight for an individual; and
    a weight management application comprising modules executable by the at least one processor to:
        receive a weight management request, the weight management request comprising current weight management data comprising body weight for a particular individual;
        retrieve a corresponding personal weight metabolism model for the particular individual from the data base in response to the management request, the personal weight metabolism model comprising an equation that calculates one or more expected weight parameter comprising expected body weight for the particular individual based on current body weight;
        calculate at least one new weight parameter comprising expected body weight for using the corresponding personal weight metabolism model based on the current body weight data;
        compare the new weight parameter to the expected parameter to determine an adherence status for the particular individual with a defined intervention program; and
        generate a feedback signal to achieve weight management comprising attaining a desired body weight for the particular individual.

2. The system of claim 1 wherein the defined intervention program is selected from the group consisting of diet intervention, exercise, psychological intervention, surgery, medication administration, alteration of sleep or circadian rhythmicity, and a combination thereof.

3. The system of claim 1 wherein the weight management data further comprises accelerometer data for the particular individual.

4. The system of claim 1 wherein the weight management request is received from a remote computing device via a communication network.

5. The system of claim 1 wherein the remote computing device is at least one member selected from a group consisting of a personal computer, a lap top computer, a personal digital assistant, an energy sensing device, a weight sensing device, and a combination thereof.

6. The system of claim 5 wherein the weight management data is supplemented by data generated by the energy sensing device, the energy sensing device providing a measurement of weight management data selected from at least one physiological measurement, at least one behavioral measurement, and a combination thereof.

7. The system of claim 5 wherein the energy sensing device provides weight management data selected from the group consisting of metabolic heat, body composition, oxygen consumption, carbon dioxide production, isotopic tracer dilution, isotopic tracer turnover, urinary metabolites, blood metabolites, blood hormone levels, physical activity, exercise, heart rate, blood pressure, food selection, diet adherence, eating behavior, step number, accelerometer data, and a combination thereof.

8. The system of claim 5 wherein the weight management data is generated by the weight sensing device.

9. The system of claim 1 wherein the modules executable by the at least one processor are further configured to transmit the feedback signal to the remote computing device via the communication network for display.

10. The system of claim 1 wherein the feedback signal to achieve weight management comprises dietary management program adjustments, required behavior adjustments, a projected weight loss trajectory range at the particular individual's current adherence status, prescriptions for specific modifications to the intervention required to achieve a desired goal weight, or a combination thereof.

11. The system of claim 1 wherein the adherence status comprises at least one of:
   a projection of whether the particular individual is on track to meet a personal weight goal; and
   one or more corrective dietary and/or physical activities to place the particular individual back on track to meet the weight goal.

12. A method for monitoring and managing the weight of an individual, comprising:
   receiving a weight management request at at least one processor, the weight management request comprising current weight management data comprising current body weight for a particular individual;
   retrieving a corresponding personal weight metabolism model for a particular individual from a data base in response to the weight management request, the data base storing a plurality of personal weight metabolism model records, each personal weight metabolism model record comprising body weight for the particular individual and corresponding to a particular mathematical model of metabolism that predicts future changes in body weight for an individual or for each of a plurality of individuals, the personal weight metabolism model comprising an equation that calculates one or more expected weight parameter comprising expected body weight for the particular individual based on current body weight;
   calculating at least one new weight parameter comprising expected body weight at the at least one processor for the corresponding personal weight metabolism model based on the current body weight;
   comparing the new weight parameter to the expected parameter at the at least one processor to determine an adherence status for the particular individual with a defined intervention program; and
   generating, at at least one processor, a feedback signal to achieve weight management comprising attaining a desired body weight for the particular individual.

13. The method of claim 12 wherein the defined intervention program is selected from the group consisting of diet intervention, exercise, psychological intervention, surgery, medication administration, alteration of sleep or circadian rhythmicity, and a combination thereof.

14. The method of claim 12 wherein the weight management data further comprises accelerometer data for the particular individual.

15. The method of claim 12 wherein the weight management data received from a weight sensing device via a communication network.

16. The method of claim 12 wherein the weight management data is received from a remote computing device via a communication network.

17. The method of claim 12 further comprising transmitting the feedback signal to the remote computing device via the communication network for display.

18. The method of claim 12 wherein the feedback signal comprises a message or generated report that informs the particular individual of required dietary management program adjustments, required behavior adjustments, a projected weight loss trajectory range at the s particular individual's current adherence status, prescriptions for specific modifications to the intervention required to achieve a desired goal weight.

19. The method of claim 12 wherein:
   the weight management request is received from and energy sensing device the via a communication network;
   the weight management data is supplemented by data generated by the energy sensing device; and
   the weight management data is selected from at least one physiological measurement, at least one behavioral measurement, or a combination thereof.

20. The method of claim 12 wherein the weight management data is selected from the group consisting of metabolic heat, body composition, oxygen consumption, carbon dioxide production, isotopic tracer dilution, isotopic tracer turnover, urinary metabolites, blood metabolites, blood hormone levels, physical activity, exercise, heart rate, blood pressure, food selection, diet adherence, eating behavior, step number, and accelerometer data, and a combination thereof.

* * * * *